US012588875B2

(12) United States Patent
Cox et al.

(10) Patent No.: US 12,588,875 B2
(45) Date of Patent: Mar. 31, 2026

(54) SYSTEM AND METHOD FOR SENSING PHYSIOLOGICAL PARAMETERS

(71) Applicant: KONINKLIJKE PHILIPS N.V., Eindhoven (NL)

(72) Inventors: Lieke Gertruda Elisabeth Cox, Eindhoven (NL); Erik Gosuinus Petrus Schuijers, Breda (NL)

(73) Assignee: KIONINKLIJKE PHILIPS N.V., Eindhoven (NL)

( * ) Notice: Subject to any disclaimer, the term of this patent is extended or adjusted under 35 U.S.C. 154(b) by 1326 days.

(21) Appl. No.: 17/312,995

(22) PCT Filed: Dec. 10, 2019

(86) PCT No.: PCT/EP2019/084301
§ 371 (c)(1),
(2) Date: Jun. 11, 2021

(87) PCT Pub. No.: WO2020/120425
PCT Pub. Date: Jun. 18, 2020

(65) Prior Publication Data
US 2022/0071570 A1    Mar. 10, 2022

(30) Foreign Application Priority Data

Dec. 14, 2018    (EP) ..................................... 18212672

(51) Int. Cl.
*A61B 5/00* (2006.01)
*A61B 5/0205* (2006.01)
(Continued)

(52) U.S. Cl.
CPC ............ *A61B 5/746* (2013.01); *A61B 5/0205* (2013.01); *A61B 5/02416* (2013.01);
(Continued)

(58) Field of Classification Search
CPC ... A61B 5/746; A61B 5/0205; A61B 5/02416; A61B 5/1118; A61B 5/1123;
(Continued)

(56) References Cited

U.S. PATENT DOCUMENTS 9,934,673 B2    4/2018  Hou
11,298,048 B2    4/2022  Van Der Hulst
(Continued)

FOREIGN PATENT DOCUMENTS

JP      57203985 A      12/1982
WO    2009112976 A1    9/2009
(Continued)

OTHER PUBLICATIONS

International Search Report and Written Opinion, International Application No. PCT/EP2019/084301, Mailed on Jan. 30, 2020.
(Continued)

*Primary Examiner* — Abid A Mustansir

(57)    ABSTRACT

A physiological parameter sensing system receives signals from (on includes) a first physiological parameter sensor and an activity monitor. The first physiological parameter signal is used to determine when additional physiological parameter sensing is recommended and an alert is then generated. The alert has characteristics which depend on the type and/or level of activity currently being undertaken by the user. In this way, the alert can be selected so that it is perceived by the user but without being an annoyance.

12 Claims, 2 Drawing Sheets

(51) Int. Cl.

| | |
|---|---|
| *A61B 5/024* | (2006.01) |
| *A61B 5/11* | (2006.01) |
| *A61B 5/361* | (2021.01) |

(52) U.S. Cl.
CPC ........... *A61B 5/1118* (2013.01); *A61B 5/1123* (2013.01); *A61B 5/361* (2021.01); *A61B 5/4812* (2013.01); *A61B 2562/0219* (2013.01)

(58) Field of Classification Search
CPC ................. A61B 5/361; A61B 5/4812; A61B 2562/0219; A61B 5/318; A61B 5/7475; A61B 5/7405; A61B 5/742; A61B 5/7455; A61B 5/02405; A61B 5/02438; A61B 5/0295; A61B 5/14552; A61B 5/6802
See application file for complete search history.

(56) References Cited

U.S. PATENT DOCUMENTS

| | | | |
|---|---|---|---|
| 2010/0076331 A1 | 3/2010 | Chan et al. | |
| 2017/0014037 A1 | 1/2017 | Coppola et al. | |
| 2017/0258349 A1* | 9/2017 | Watanabe ............ | A61B 5/0245 |
| 2021/0084403 A1* | 3/2021 | Hviid ...................... | G06F 3/044 |

FOREIGN PATENT DOCUMENTS

| | | |
|---|---|---|
| WO | 2012140559 A1 | 10/2012 |
| WO | 2015002945 A2 | 1/2015 |
| WO | 2017112412 A1 | 6/2017 |

OTHER PUBLICATIONS

Reliable PPG-based algorithm in atrial fibrillation detection. Shan, SM, et al. 2016. Biomedical Circuits & Systems.
Photoplethysmography-Based System for Atrial Fibrillation Detection During Hemodialysis. Stankevicius, D, et al. 2016. XIV Mediterranean Conference on Medical and Biological Engineering and Computing . pp. 79-82.

* cited by examiner

SYSTEM AND METHOD FOR SENSING PHYSIOLOGICAL PARAMETERS

This application is the U.S. National Phase application under 35 U.S.C. § 371 of International Application No. PCT/EP2019/084301, filed on 10 Dec. 2019, which claims the benefit of European Application Serial No. 18212672.2, filed 14 Dec. 2018. These applications are hereby incorporated by reference herein.

FIELD OF THE INVENTION

This invention relates to a system and method for sensing a physiological parameter of a subject, in particular a system and method suitable for continuous monitoring.

BACKGROUND OF THE INVENTION

Physiological parameters of a person, for example the heart rate (HR), the respiration rate (RR) or the arterial blood oxygen saturation (SpO$_2$), serve as indicators of the current state of a person and as powerful predictors of serious medical events. For this reason, physiological parameters are extensively monitored in inpatient and outpatient care settings, at home or in further health, leisure and fitness settings.

One way of measuring physiological parameters is plethysmography. Plethysmography generally refers to the measurement of volume changes of an organ or a body part and in particular to the detection of volume changes due to a cardiovascular pulse wave traveling through the body of a subject with every heartbeat.

Photoplethysmography (PPG) is an optical measurement technique that evaluates a time variant change of light reflectance or transmission of an area or volume of interest. PPG is based on the principle that blood absorbs light more than surrounding tissue, so variations in blood volume with every heart beat affect transmission or reflectance correspondingly.

Thus, a PPG signal conveys heart rate information. In addition to information about the heart rate, a PPG waveform can comprise information attributable to other physiological phenomena such as respiration. By evaluating the transmittance and/or reflectivity at different wavelengths (typically red and infrared), the blood oxygen saturation can be determined. PPG signals may also be used to provide an indicator of arrhythmia and other cardiac conditions.

However, ECG measurement is the standard technology for diagnosing cardiac arrhythmia. Long-term continuous ECG monitoring until arrhythmia is diagnosed is however not always feasible.

As alternative, it is known that a combination of continuous PPG monitoring and ECG spot measurements can be used. In this solution, a PPG sensor can be embedded in a wearable, which is for example worn on the wrist. An algorithm detects possible arrhythmia episodes based on the PPG signal and then alerts patients to take an ECG measurement that can be used for diagnosis. This alert can be given by the wearable for example using vibration, sound, or light signals, or a combination thereof.

In order for the device to be effective, the response rate of the user to an alert should be as high as possible. It is for example important that the user responds, and preferably rapidly, to capture short-duration arrhythmia episodes.

Known devices allow users to manually personalize the alerts and mode of operation depending on the environment and circumstances. For instance, a vibration signal is preferred to provide the alert when watching a movie. Especially during sleep, alerts are likely to be missed.

If the alert is set to be strong, it may be perceived as obtrusive, not only for the user, but possibly also to the people around him/her. For example, it may disturb a meeting, or at night it may wake up the user's spouse as well.

US 2017/0258349 discloses a watch based ECG monitoring system. Pulse wave monitoring is performed, and when the need for an ECG measurement is determined, an output notification is provided. In particular, if an arrhythmia is detected based on the pulse wave monitoring, a notification is provided to the user to perform an ECG measurement.

US 2017/0014037 discloses a system for detecting a heart rate variability using a PPG sensor, and then initiating an instruction to the user to perform an ECG measurement. An accelerometer is used to correct for motion artefacts in the PPG signal.

US 2010/0076331 discloses another watch based ECG monitoring system. The user is reminded to make an ECG measurement based on activity levels and temperature changes.

There is therefore a need for a more reliable system of alerts, in particular for alerts which relate to physiological measurements.

SUMMARY OF THE INVENTION

The invention is defined by the claims.

According to an aspect of the invention, there is provided a physiological parameter sensing system, comprising:

a controller, wherein the controller is adapted to:

receive activity signals from at least one activity monitor and physiological signals from at least one first physiological parameter sensor;

analyze the activity signals to determine a type and/or level of activity;

analyze physiological signals to determine when additional physiological parameter sensing is recommended; and in response to the determination, generate an alert signal for creating an alert having characteristics which depend on the type and/or level of activity.

This system uses signals from a first sensor to determine when further investigations are needed. The first sensor is for example suitable for long term continuous monitoring, for example including during sleep and during exercise, whereas the further investigations may require sensing using a more accurate sensing modality but one which may not be suitable for continuous monitoring. The further investigations are for example intended to provide information of diagnostic relevance.

The alert advises the user that the further investigations should be carried out. However, the alert takes account of the current activity of the user, so that it can be selected to be suitable for obtaining the user's attention as well as not excessively disturbing the user.

The system may further comprise an input device for receiving a user input in response to a generated alert, and wherein the controller is further adapted to measure the time which elapses between the generation of the alert and the received response of the user to the generated alert.

This timing information may be used to represent the effectiveness of the alert to that particular user. In this way, the alert characteristics may be personalized to a particular user based on their response to the alert. The controller for example has a timer or controls a timer, so that timing is initiated when the alert is generated and timing is ended when the user response is received.

The input device for example comprises elements for allowing an instruction to stop the alert. Thus, the response time is the time taken for the user to perceive the alert and then provide an instruction for the alert to stop. If the user knows to stop the alert as soon as it is perceived, this becomes a suitable measure of how effective the alert has been.

The system for example has a memory storing a mapping between types (i.e. categories) of activity and/or intensity of activities of a given type and alert characteristics so that the alert characteristics are chosen automatically based on the determined activity type and/or level. The controller may then be adapted to update this mapping based on the timed responses.

However, the system may include additional ways of changing the alert characteristics, other than based on the timing of the user's response. For example the user may be able to personalize their alert settings in other ways by providing user input. The user may for example tune differently the characteristics of different types of alert. This user adjustability may be an alternative option to allow manual setting by the user of the alert characteristics (depending on activity type) it may combine with the automatic adjustment of the alert characteristics based on the timed response.

A machine learning algorithm may be used for this purpose, to optimize the alert characteristics. This is based on a statistical analysis of the response times of the user for the different alert characteristics. The alert should be as minimally disruptive as possible while achieving a desired response speed.

The instruction to stop the alert may also be used to start the further physiological parameter sensing, if the further sensing is part of the same overall system. Thus, the user may be required to perform the further measurement as soon as the alert is perceived.

The alert characteristics for example comprise:
a type of alert selected from at least a vibration, a sound and light; and/or
an intensity and/or duration of a generated alert signal.

The intensity of a sound alert is the volume, the intensity of vibration alert is the vibration magnitude, and the intensity of a light alert is the light intensity. The alert may combine different types (e.g., vibration and sound) and different intensities. The frequency of a vibration may be adjusted, and the alert may be pulsed, with the timing controlled (e.g. regular or irregular) to achieve a desired response. Different combinations of alert types and alert intensities may be combined based on the activity information.

The first physiological parameter signal for example comprises a photoplethysmography, PPG, signal. This may be used at least to obtain heart rate information, but it may additionally enable arrhythmia to be detected. PPG sensing can be carried out continuously, during sleep and when performing activities. However, other wearable sensors may be used for continuous cardiac information monitoring, such as accelerometers.

The controller is for example adapted to analyze the physiological sensor signals to identify an abnormal vital sign thereby to determine when additional physiological parameter sensing is recommended. The abnormal vital sign may be arrhythmia, for example atrial fibrillation.

The controller is for example arranged to receive and analyze and activity signal comprising an accelerometer signal (from one or more accelerometers) and/or other inertial signals such as from one or more gyroscopes and/or one or more magnetometers. It is well known that acceleration information can be used to categorize the activity of a user.

The activity signals for example comprise at least two different activity types selected from active, sedentary, sleeping, running, walking, cycling, and sleeping in a specific sleep stage. Thus, at a general level, the activities may be categorized as active, sedentary (but awake) or asleep. However, more detailed activities may be identified (running, walking, cycling etc.) and specific sleep stages may be identified (REM and non-REM, or specific sleep stages such as REM, N1, N2, N3).

The system may include the various sensors. Thus the system may further comprise at least one of the following:
a first physiological parameter sensor, for example a PPG sensor, which is arranged to provide a physiological signal when interacting with a patient;
an activity monitor which provides an activity signal when interacting with the patient;
an alert generating unit to generate an alert based on the alert signal.

The system may further comprise an ECG sensor, wherein the additional physiological parameter sensing comprises ECG sensing. Thus, the ECG sensor is ready to be used by the user as soon as an alert is provided. It may be important to take an ECG measurement as soon as an alert is provided, since the issue to be investigated may be short-lived. An ECG sensor for example comprises electrodes for application against the skin for detecting electrical signals produced by the subject's heart each time it beats.

The invention also provides a method of generating an alert in response to sensing of a physiological parameter, comprising:
monitoring a physiological parameter using a first physiological parameter sensor;
analyzing the physiological parameter to determine when additional physiological parameter sensing is recommended;
monitoring an activity of a user to determine a type and/or level of activity; and
in response to the determination, generating an alert having characteristics which depend on the type and/or level of activity.

The method may comprise receiving a user input in response to a generated alert, and timing the response of the user to a generated alert, wherein the method further comprises updating a mapping between the alert characteristics and the type and/or level of activity based on the timed response.

The first physiological parameter sensor is for example a PPG sensor and the analyzing comprises identifying arrhythmia (such as atrial fibrillation), and wherein the additional physiological parameter sensing comprises ECG sensing.

The invention also provides a computer program product comprising computer program code, adapted to, when run on a computer, cause the computer to carry out the method defined above.

BRIEF DESCRIPTION OF THE DRAWINGS

Preferred embodiments of the invention will now be described in detail, by way of example only, with reference to the accompanying drawings, in which.

DETAILED DESCRIPTION OF THE EMBODIMENTS

Figure 1:
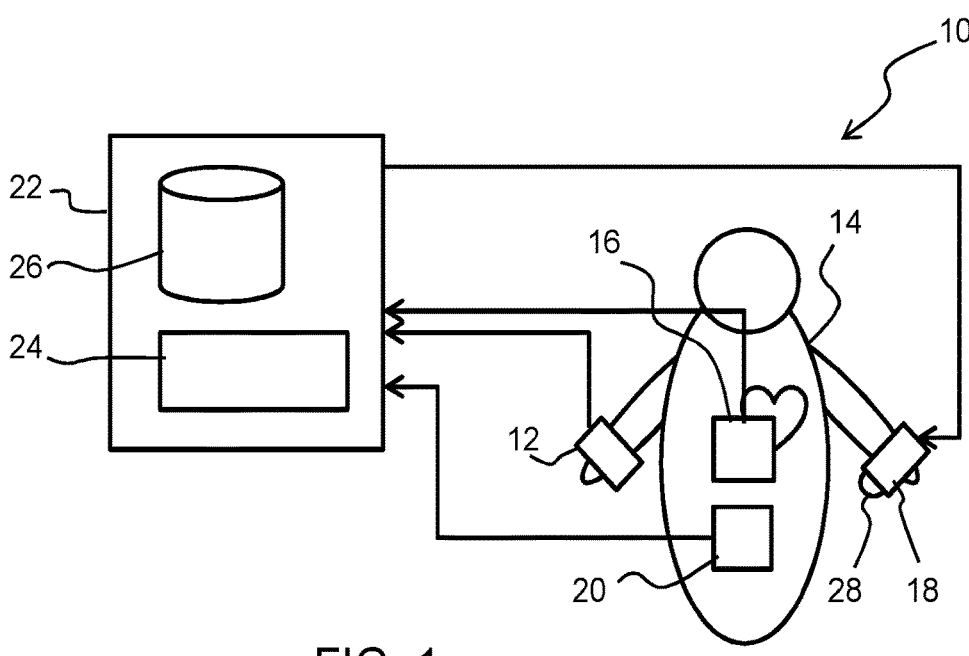
FIG. 1 shows a physiological parameter sensing system.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a physiological parameter sensing system which receives signals from (or includes) a first physiological parameter sensor and an activity monitor. The first physiological parameter sensor signal is used to determine when additional physiological parameter sensing is recommended and an alert is then generated. The alert has characteristics which depend on the type and/or level of activity currently being undertaken by the user. In this way, the alert can be selected so that it is perceived by the user but without being an annoyance.

FIG. 1 shows an example of a physiological parameter sensing system 10. In this example, all associated sensors are shown as part of the system. However, the invention may be implemented only by a controller which receives and processes signals from external sensors.

A first physiological parameter sensor 12 is for detecting an abnormal vital sign of a user 14. The sensor 12 is typically a wearable sensor for continuous monitoring of a physiological parameter so that it can be used during the day and at night, and also while the user is engaged in physical activity such as running or cycling or playing sport. It is used to determine when additional physiological parameter sensing is recommended. This may be desired because more accurate diagnosis is possible from a different sensing modality but typically one which is not suitable for continuous monitoring.

In a preferred example the first physiological parameter sensor is a photoplethysmography, PPG, sensor. This may be used at least to obtain heart rate information, but it may additionally enable arrhythmia such as atrial fibrillation to be detected. The PPG sensor is for example a wrist worn device.

The invention may be applied to other sensor examples. In all cases, The vital sign information obtained by the first physiological parameter sensor may not be the best possible sensing modality for making a diagnosis, so is only used to provide an indication (in particular an alert) of when a more suitable sensing modality should be used. For example, the first physiological parameter sensor may analyze the cardiac performance based on movement detection rather than optical detection as used by a PPG sensor. The PPG sensor may be a contact sensor or a remote sensor, for example using a camera.

A second physiological sensor 16 is used to perform the additional physiological sensing.

In a preferred example, the second physiological parameter sensor is an ECG sensor. Thus, the ECG sensor 16 is ready to be used by the user as soon as an alert is provided. It may be important to take an ECG measurement as soon as an alert is provided, since the issue to be investigated may be short-lived.

The ECG sensor 16 for example comprises electrodes applied against the skin for detecting electrical signals produced by the subject's heart each time it beats. The ECG sensor may be part of a patch or a chest-worn belt.

The second physiological parameter sensor may instead not be a worn sensor, and may be an external device which is not integrated into the overall system. Instead, the user may need to apply the second physiological parameter sensor before making the further measurement. This may depend on the speed with which the further measurement need to be taken. A fully integrated system as shown in FIG. 1 provides a fully integrated solution which enables the second physiological parameter sensor to be operated as soon as an alert is received.

In another example, the second physiological parameter sensor is a blood pressure monitor. Blood pressure (in particular blood pressure differences) can be derived from a PPG signal, but not with very high accuracy. PPG-based measurements using the first physiological parameter sensor may be used to provide an alert (for example for subjects on blood pressure medication or a pregnant woman at risk of preeclampsia) to take a more accurate blood pressure measurement with a blood pressure monitor, such as a cuff.

The invention could also be applied to core body temperature measurement. For example, the first physiological parameter sensor may be a temperature sensor worn on the wrist, which can offer some indication of core body temperature. This may be relevant to measure fevers or infection. For a more accurate measurement after an alert has been given, a thermometer could be used.

An alert generating unit 18 is used to alert the user to the need to perform the additional physiological parameter sensing.

The alert generating unit 18 may use vibration, sound or light, or any combination of these to provide a signal which will be perceived by the user. The alert generated has alert characteristics, by which is meant a type of alert (vibration, sound and light) and/or an intensity of a generated alert signal and/or duration of a generated alert signal. The alert generating unit may have only one type, such as vibration only, in which case the alert characteristics relate only to the nature of the vibrations generated.

In the example shown, the alert generating unit is shown as a wrist worn device, which provides a vibration, and optionally also outputs a sound (although a sound may be generated by other parts of the system). The alert may additionally or alternatively be generated by an external device under the instruction/control of the alert generating unit, such as a television, mobile phone or tablet of the user.

The intensity of a sound alert is the volume, the intensity of a vibration alert is the vibration magnitude, and the intensity of a light alert is the light intensity. The alert may combine different types (e.g., vibration and sound) and different intensities.

The alert generating unit 18 is shown separate to the sensors 12, 16 but it may of course be integrated with one (or both) of the sensors.

The invention is based on controlling the alert generating unit 18 to generate an alert having characteristics which depend on a type and/or level of activity currently undertaken by the user. For this purpose, the system has an activity monitor 20.

The activity monitor 20 for example comprises an accelerometer arrangement (of one or more accelerometers) for detecting movements of the subject. It is well known that acceleration information can be used to categorize the activity of a user.

The activity monitor 20 is for example for detecting at least two different activity types, so that different alerts may be generated from the different activity types.

There may be a small number of different activity types such as active, sedentary (but awake) or sleeping.

However, the activity types may be categorized more finely such as running, walking, cycling, dancing.

There may be only one activity type, and the activity is categorized based on the intensity of the activity.

The detection of sleeping may also be divided into sleep stages. In particular, sleep may be generally categorized as rapid eye movement (REM) sleep and non-rapid eye movement (non-REM) sleep. The non-REM sleep may further be categorized as stage N1, stage N2, or stage N3 sleep. N1 corresponds to a light sleep state and N3 corresponds to a deep sleep state. Non-REM stage N3 or stage N2 sleep may be slow wave (e.g., deep) sleep. Sleep stage determination has been shown based on PPG measurements, as reported in "Validation of Photoplethysmography-Based Sleep Staging Compared With Polysomnography in Healthy Middle-Aged Adults", Fonseca P et. al., Sleep 2017 Jul. 1; 40(7).

The various control functions are implemented by a controller 22. The controller 22 comprises a processing unit 24 and a memory 26.

The controller 22 analyzes the signals from the activity monitor 20 to determine a type and/or level of activity. It may additionally determine activity intensity levels of a particular activity.

The signals from the first physiological parameter sensor 12 are analyzed to determine when the additional physiological parameter sensing is recommended, namely when the abnormal vital sign is detected.

The alert generator is then employed to generate the most appropriate alert signal. In particular, the memory 26 stores a mapping between types and/or levels of activity and alert characteristics so that the alert characteristics are chosen automatically based on the determined activity type and/or level. This mapping may be an algorithm or a look up table.

Thus, overall the system uses the first sensor 12 to determine when further investigations are needed. The first sensor performs for long term continuous monitoring, whereas the further investigations may require sensing using a more accurate sensing modality but one which may not be suitable for continuous monitoring.

The system of FIG. 1 further comprises an input device 28 for receiving a user input in response to a generated alert. As shown, it may be part of the alert generating unit 18, such as a push button.

The controller 22 times the response of the user to a generated alert, i.e. the time between the outputting of the alert and the user operating the input device 28. This timing information may be used to represent the effectiveness of the alert to that particular user, and while they are involved in the particular detected type and/or level of activity. In this way, the alert characteristics may be personalized to a particular user based on their response to the alert.

This characterization involves updating the mapping stored in the memory, or else it may involve learning by the algorithm used to implement the mapping based on the activity type and response times. The most suitable alert characteristics are for example determined based on training of the algorithm and/or subsequent learning during use of the system.

The machine learning may implement deep learning, the available the raw data being processed to determine when to trigger an alert.

The user for example uses the input device 18 to stop the alert. Thus, the response time is the time taken for the user to perceive the alert and then provide an instruction for the alert to stop.

The instruction to stop the alert may also be used to start the further physiological parameter sensing using the second physiological parameter sensor 16 (when this is an integrated part of the overall system, as in FIG. 1). Thus, the user may be required to perform the further measurement as soon as the alert is perceived.

The response rate of the user should be as high as possible to ensure the second physiological parameter sensing is performed as soon as it is necessary. This will allow capture of short-duration arrhythmia episodes.

The invention provides alert settings, for example different vibration characteristics of a vibration alert, which are adapted at least to the current activity circumstances of the user and optionally also to the characteristics of the user. Typically, the intensity of the vibration alert is adjusted in such a way that the alert is weak when the person is sedentary and strong when the person is active. In addition, to allow for proper waking during sleep, the alert could be adapted based on the detected sleep stage as mentioned above. Depending on the subject's medical condition, the alert may be ignored during sleep as this may be beneficial for the overall health of the subject.

If the person is in deep sleep, he/she will require a stronger alert than when during light sleep. In addition or alternatively, the rhythmic pattern of the alert may be adjusted, e.g. making it less regular when a person is active. The length of the alert may also be adjusted, e.g. longer bursts or the non-response time may be adjusted, e.g. keeping it on longer when the person is active.

The response statistics that are required for determining the suitable alert settings for example typically consist of the average response time, optionally also activity-type dependent, or the number of non-responses, again optionally also activity-type dependent.

If the subject reacts relatively late (on average) to an alert, the alert will be intensified, or made less regular or made longer. If the person reacts quickly (on average) to an alert, the alert may be reduced or made more regular or made shorter.

It is noted that algorithms are known for detecting arrhythmia from PPG-signals, for example reference is provided to "Reliable PPG-based algorithm in atrial fibrillation detection" Shan, S M, et al. 2016. Biomedical Circuits & Systems, and "Atrial Fibrillation Detection using Photoplethysmography and Acceleration Data at the Wrist" Bonomi A G et. al., Computing in Cardiology 2016, vol. 43.

The examples above are based on controlling the alert based on activity information. Other measurements may be taken into account as well. For example, an ambient light sensor may be used to detect darkness which may for example indicate coverage of the alert device by clothing. Thus, a vibration and/or sound may be preferred to a light output. Similarly, if there is a lot of ambient noise detected by microphone, a vibration and/or light may be preferred to a sound output.

For some activities, the alert adaptation may be configurable. For example, in some cases (e.g. set by the user) it may be determined that sleep could be undisturbed (as mentioned above) so that no alert is given, whereas in the other cases, it may be desired to wake the subject from sleep, and the alert characteristics are chosen accordingly. In this way, there may be configuration settings that can be enabled by the user and/or the physician.

In the examples above, the activity monitor and the first physiological parameter sensor are different units. However, in some examples they may be the same unit. For example, the PPG sensor may be used to obtain activity information, for example based on the heart rate and respiration rate.

Figure 2:
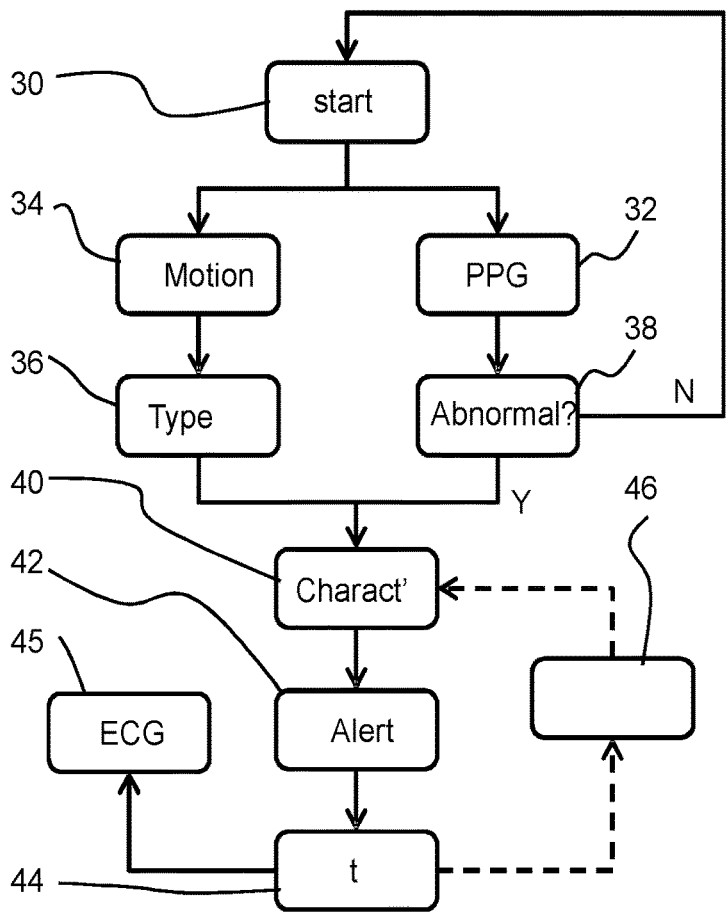
FIG. 2 shows a physiological parameter sensing method.

FIG. 2 shows a method of generating an alert in response to sensing of a physiological parameter.

The method starts in step 30.

In parallel, there is continuous monitoring of a physiological parameter using a first physiological parameter sensor in step 32 and monitoring an activity of a user in step 34.

In step 36, the activity of the user is analyzed to determine a type and/or level of activity. In step 38, the physiological parameter is analyzed to determine when additional physiological parameter sensing is recommended. If not, the method can return to the start, so that there is continuous PPG monitoring until an abnormal vital sign is detected.

In step 40, the alert characteristics are determined by the controller, and these will depend on the type of activity and/or the intensity of activity.

In step 42 the alert is generated.

This provides a method which takes account of at least the activity type and/or level of the user.

Optionally, there is further personalization, whereby in step 44, a user input is received in response to the generated alert. This response triggers sensing using the second physiological parameter sensor (i.e. the ECG sensor) in step 45, and the response of the user to the generated alert is also timed by the controller. The method may return to the start automatically after the ECG measurement, or the user may restart the device into its monitoring mode (using the first physiological parameter sensor).

The timing information is used by the controller to update the mapping between the alert characteristics and the type and/or level of activity, as shown by feedback step 46.

The invention is implemented at least in part in software, by software operating the controller.

Figure 3:
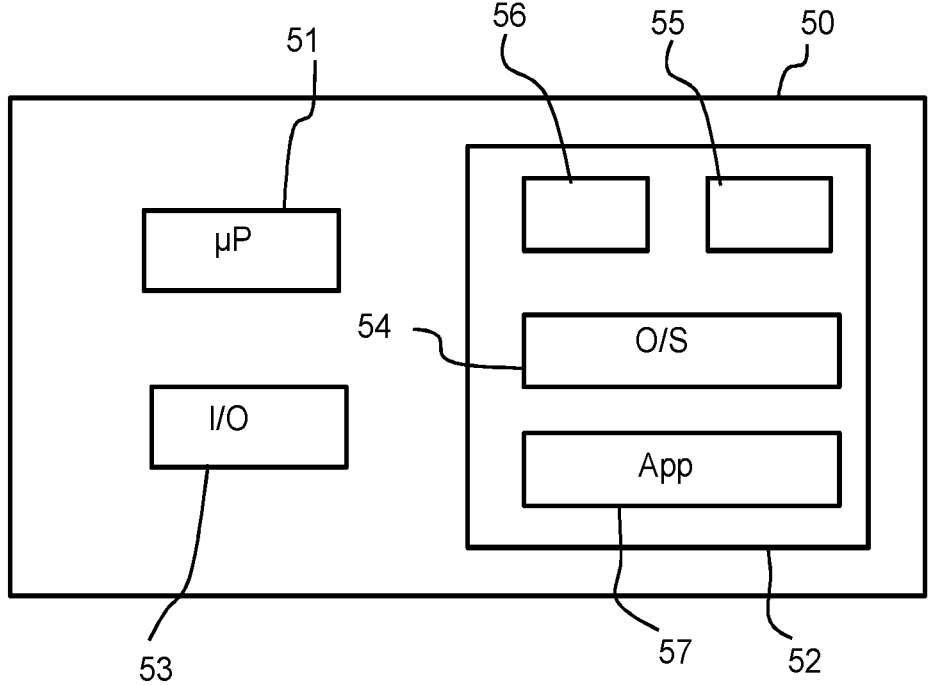
FIG. 3 shows a generic computer architecture for implementing the controller of the system of FIG. 1.

FIG. 3 illustrates an example of a computer 50 for implementing the controller described above.

The computer 50 may include one or more processors 51, memory 52, and one or more I/O devices 53 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 51 is a hardware device for executing software that can be stored in the memory 52. The processor 51 can be virtually any custom made or commercially available processor, a central processing unit (CPU), a digital signal processor (DSP), or an auxiliary processor among several processors associated with the computer 50, and the processor 51 may be a semiconductor based microprocessor (in the form of a microchip) or a microprocessor.

The memory 52 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 52 may incorporate electronic, magnetic, optical, and/or other types of storage media. Note that the memory 52 can have a distributed architecture, where various components are situated remote from one another, but can be accessed by the processor 51.

The software in the memory 52 may include one or more separate programs, each of which comprises an ordered listing of executable instructions for implementing logical functions. The software in the memory 52 includes a suitable operating system (O/S) 54, compiler 55, source code 56, and one or more applications 57 in accordance with exemplary embodiments.

The application 57 comprises numerous functional components such as computational units, logic, functional units, processes, operations, virtual entities, and/or modules.

The operating system 54 controls the execution of computer programs, and provides scheduling, input-output control, file and data management, memory management, and communication control and related services.

Application 57 may be a source program, executable program (object code), script, or any other entity comprising a set of instructions to be performed. When a source program, then the program is usually translated via a compiler (such as the compiler 55), assembler, interpreter, or the like, which may or may not be included within the memory 52, so as to operate properly in connection with the operating system 54. Furthermore, the application 57 can be written as an object oriented programming language, which has classes of data and methods, or a procedure programming language, which has routines, subroutines, and/or functions, for example but not limited to, C, C++, C #, Pascal, BASIC, API calls, HTML, XHTML, XML, ASP scripts, JavaScript, FORTRAN, COBOL, Perl, Java, ADA, .NET, and the like.

The I/O devices 53 may include input devices such as, for example but not limited to, a mouse, keyboard, scanner, microphone, camera, etc. Furthermore, the I/O devices 53 may also include output devices, for example but not limited to a printer, display, etc. Finally, the I/O devices 53 may further include devices that communicate both inputs and outputs, for instance but not limited to, a network interface controller (NIC) or modulator/demodulator (for accessing remote devices, other files, devices, systems, or a network), a radio frequency (RF) or other transceiver, a telephonic interface, a bridge, a router, etc. The I/O devices 53 also include components for communicating over various networks, such as the Internet or intranet.

When the computer 50 is in operation, the processor 51 is configured to execute software stored within the memory 52, to communicate data to and from the memory 52, and to generally control operations of the computer 50 pursuant to the software. The application 57 and the operating system 54 are read, in whole or in part, by the processor 51, perhaps buffered within the processor 51, and then executed.

When the application 57 is implemented in software it should be noted that the application 57 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If the term "adapted to" is used in the claims or description, it is noted the term "adapted to" is intended to be equivalent to the term "configured to". Any reference signs in the claims should not be construed as limiting the scope.

The invention claimed is:

1. A physiological parameter sensing system, comprising:
at least one first physiological parameter sensor;
at least one activity monitor;
a controller, wherein the controller is adapted to:
  receive physiological signals from the at least one first physiological parameter sensor;
  analyze the physiological signals to identify an abnormal vital sign thereby to determine when additional physiological parameter sensing is recommended;
  receive activity signals from the at least one activity monitor;
  analyze the activity signals to determine a type and/or level of activity; and
  in response to the determinations, generate an alert signal for creating an alert having characteristics that depend on the type and/or level of activity,
    wherein the alert is configured to obtain the attention of a user; and
an input device for receiving a user input in response to a generated alert;
wherein the controller is further adapted to measure the time which elapses between the generation of the alert and the received response of the user to the generated alert.

2. The system of claim 1, wherein the system stores a mapping between (i) alert characteristics and (ii) types and/or levels of activity.

3. The system of claim 1, wherein the system stores a mapping between (i) alert characteristics and (ii) types and/or levels of activity, and wherein the controller is adapted to update the mapping based on the measured times.

4. The system of claim 1, wherein the alert characteristics comprise:
a type of alert selected from at least a vibration, a sound and/or light; and/or
an intensity and/or duration of a generated alert.

5. The system of claim 1, wherein the controller is arranged to receive and analyze physiological signals comprising a photoplethysmography (PPG) signal.

6. The system of claim 1, wherein the controller is arranged to receive and analyze an activity signal comprising an accelerometer signal.

7. The system of claim 1, wherein the activity signals comprise at least two different activity types selected from active, sedentary, sleeping, running, walking, cycling, and sleeping in a specific sleep stage.

8. The system of claim 1, further comprising at least one of the following:
a first physiological parameter sensor which is arranged to provide a physiological signal when interacting with a patient;
an activity monitor which provides an activity signal when interacting with the patient;
an alert generating unit to generate an alert based on the alert signal.

9. The system of claim 8, further comprising an ECG sensor, wherein the additional physiological parameter sensing comprises ECG sensing.

10. A method of generating an alert in response to sensing of a physiological parameter, comprising:
monitoring a physiological parameter using a first physiological parameter sensor;
analyzing the physiological parameter to identify an abnormal vital sign thereby to determine when additional physiological parameter sensing is recommended;
monitoring an activity of a user using an activity monitor to determine a type and/or level of activity;
in response to the determinations, generating an alert having characteristics that depend on the type and/or level of activity, wherein he alert is configured to obtain the attention of a user;
receiving a user input in response to a generated alert; and
measuring the time which elapses between the generation of the alert and the response of the user to the generated alert;
wherein the method further comprises updating a mapping between the alert characteristics and the type and/or level of activity based on the timed response.

11. The method of claim 10, wherein the first physiological parameter sensor is a PPG sensor and the analyzing comprises identifying arrhythmia, and wherein the additional physiological parameter sensing comprises ECG sensing.

12. A non-transitory storage medium comprising computer program code, adapted to cause a controller to carry out the method of claim 10, wherein the controller is adapted to:
receive physiological signals from the at least one first physiological parameter sensor;
analyze the physiological signals to identify the abnormal vital sign thereby to determine when the additional physiological parameter sensing is recommended;
receive the activity signals from the at least one activity monitor;
analyze the activity signals to determine the type and/or level of activity;
in response to the determinations, generate the alert signal for creating the alert having characteristics that depend on the type and/or level of activity, wherein the alert is configured to obtain the attention of a user; and
measure the time which elapses between the generation of the alert and the received response of the user to the generated alert.

* * * * *